(12) United States Patent
Derosa et al.

(10) Patent No.: US 9,756,872 B2
(45) Date of Patent: Sep. 12, 2017

(54) SUBSTITUTED BUTANOL DERIVATIVES AND THEIR USE AS FRAGRANCE AND FLAVOR MATERIALS

(71) Applicant: TAKASAGO INTERNATIONAL CORPORATION, Tokyo (JP)

(72) Inventors: Frank Derosa, Belle Mead, NJ (US); Michael E. Lankin, High Bridge, NJ (US); Andrew T. Lupo, Emerson, NJ (US)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 0 days.

(21) Appl. No.: 14/714,010

(22) Filed: May 15, 2015

(65) Prior Publication Data

US 2015/0245641 A1   Sep. 3, 2015

Related U.S. Application Data

(60) Division of application No. 12/981,758, filed on Dec. 30, 2010, now Pat. No. 9,060,535, which is a continuation of application No. PCT/US2008/068781, filed on Jun. 30, 2008.

(51) Int. Cl.

| | | |
|---|---|---|
| *C11B 9/00* | (2006.01) | |
| *A61Q 13/00* | (2006.01) | |
| *A23L 1/226* | (2006.01) | |
| *A61K 8/33* | (2006.01) | |
| *A61K 8/37* | (2006.01) | |
| *A61K 8/39* | (2006.01) | |
| *A61Q 5/02* | (2006.01) | |
| *A61Q 11/00* | (2006.01) | |
| *A61Q 19/10* | (2006.01) | |
| *A61K 47/08* | (2006.01) | |

(Continued)

(52) U.S. Cl.
CPC ............ *A23L 1/22642* (2013.01); *A23L 2/56* (2013.01); *A23L 27/20* (2016.08); *A23L 27/2028* (2016.08); *A61K 8/33* (2013.01); *A61K 8/37* (2013.01); *A61K 8/39* (2013.01); *A61K 47/08* (2013.01); *A61K 47/14* (2013.01); *A61Q 5/02* (2013.01); *A61Q 11/00* (2013.01); *A61Q 13/00* (2013.01); *A61Q 19/10* (2013.01); *C07C 43/11* (2013.01); *C07C 43/15* (2013.01); *C07C 47/198* (2013.01); *C07C 69/003* (2013.01); *C07C 69/708* (2013.01); *C07C 69/96* (2013.01); *C11B 9/0015* (2013.01); *C11B 9/0019* (2013.01); *C11D 3/2068* (2013.01); *C11D 3/2072* (2013.01); *C11D 3/2093* (2013.01); *C11D 3/50* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 4,124,644 A | 11/1978 | Sprecker et al. | |
| 4,990,697 A | 2/1991 | Renge et al. | |

(Continued)

FOREIGN PATENT DOCUMENTS

| | | |
|---|---|---|
| EP | 1 342 717 A1 | 9/2003 |
| JP | S54 12307 | 1/1979 |

(Continued)

OTHER PUBLICATIONS

Eliel, et al., "Neighboring group participation by oxygen in the solvolysis of acyclic gamma-alkoxy substituted p-toluenesulfonates", The Journal of Organic Chemistry, vol. 50, No. 15, 1985, pp. 2707-2711, XP55180874.

Extended European Search Report dated Aug. 18, 2015 in Application No. 08772254.2.

Kim, et al., "Synthesis of New-Donor-functionalized Alcohols as Organic Ligands for Metal Precursors of Metal Organic Chemical Vapor Deposition", Bulletin of the Korean Chemical Society, vol. 26, No. 5, 2005, pp. 829-832, XP55181054.

Mironov, et al., "Hydrosilylation of 4,4-dimethyl-1,3-dioxane", Journal of General Chemistry USSR, vol. 51, No. 12, 1981, pp. 2329-2332, XP009183587.

(Continued)

*Primary Examiner* — Theodore R West
(74) *Attorney, Agent, or Firm* — Baker Botts L.L.P.

(57) ABSTRACT

The present invention is related to substituted butanol derivatives of the formula:

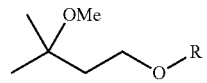

wherein R is an unsubstituted or substituted $C_{1-6}$ straight chain alkyl, an unsubstituted or substituted $C_{3-6}$ branched chain alkyl, an unsubstituted or substituted $C_{3-6}$ straight chain alkenyl, an unsubstituted or substituted $C_{3-6}$ branched chain alkenyl, an unsubstituted or substituted $C_{3-6}$ cycloalkyl, an unsubstituted or substituted $C_{1-6}$ alkoxy, nitrile, halo, amino, an unsubstituted or substituted $C_{1-6}$ alkylamino, an unsubstituted or substituted $C_{1-6}$ dialkylamino, carboxy-$C_{1-6}$ alkylamino, carboxy-$C_{1-6}$ dialkylamino, an unsubstituted or substituted acetoxy, carboxy, an unsubstituted or substituted carboxyethyl, an unsubstituted or substituted $C_{1-6}$ alkylcarbonyl, an unsubstituted or substituted $C_{1-6}$ alkylcarboxy, an unsubstituted or substituted $C_{1-6}$ alkylthio, an unsubstituted or substituted $C_{1-6}$ alkyloxy, carboxamido, an unsubstituted or substituted $C_{1-6}$ alkylcarboxamido or an unsubstituted or substituted $C_{1-6}$ dialkylcarboxamido. Such compounds are useful in flavor or flavor compositions.

7 Claims, No Drawings

(51) Int. Cl.
- *A61K 47/14* (2017.01)
- *C07C 69/003* (2006.01)
- *C07C 69/708* (2006.01)
- *C07C 69/96* (2006.01)
- *C07C 43/11* (2006.01)
- *C07C 43/15* (2006.01)
- *C07C 47/198* (2006.01)
- *C11D 3/50* (2006.01)
- *A23L 2/56* (2006.01)
- *C11D 3/20* (2006.01)
- *A23L 27/20* (2016.01)

(56) References Cited

U.S. PATENT DOCUMENTS

| | | | |
|---|---|---|---|
| 5,081,104 A | 1/1992 | Orson et al. | |
| 6,207,857 B1 | 3/2001 | Anderson et al. | |
| 9,060,535 B2 | 6/2015 | Derosa et al. | |
| 2006/0210508 A1* | 9/2006 | Gamez-Garcia | A61K 8/042 424/70.11 |
| 2008/0319088 A1 | 12/2008 | Smith et al. | |

FOREIGN PATENT DOCUMENTS

| | | |
|---|---|---|
| JP | S59 166600 A | 9/1984 |
| WO | WO 2004/050595 A1 | 6/2004 |
| WO | WO 2005/100869 A1 | 10/2005 |

OTHER PUBLICATIONS

Traeger, et al., "Activation Barriers for Addition of Methyl Radicals to Oxygen-Stabilized Carbocations", The Journal of Physical Chemistry A, vol. 109, No. 45, 2005, pp. 10467-10473, XP55180915.
U.S. Appl. No. 12/981,758, Oct. 18, 2012 Non-Final Office Action.
U.S. Appl. No. 12/981,758, Jan. 18, 2013 Response to Non-Final Office Action.
U.S. Appl. No. 12/981,758, Apr. 5, 2013 Final Office Action.
U.S. Appl. No. 12/981,758, Jul. 2, 2013 Amendment and Request for Continued Examination (RCE).
U.S. Appl. No. 12/981,758, Sep. 24, 2014 Non-Final Office Action.
U.S. Appl. No. 12/981,758, Dec. 19, 2014 Response to Non-Final Office Action.
U.S. Appl. No. 12/981,758, Feb. 18, 2015 Notice of Allowance.
U.S. Appl. No. 12/981,758, May 15, 2015 Issue Fee Payment.
International Search Report for International Application No. PCT/US2008/068781, filed Jun. 30, 2008.

* cited by examiner

SUBSTITUTED BUTANOL DERIVATIVES AND THEIR USE AS FRAGRANCE AND FLAVOR MATERIALS

CROSS-REFERENCE TO RELATED APPLICATIONS

This application is a divisional of and claims priority to U.S. patent application Ser. No. 12/981,758, filed Dec. 30, 2010, which is a continuation of International Application No. PCT/US2008/068781, filed Jun. 30, 2008, which is incorporated by reference in its entirety herein, and from which priority is claimed.

FIELD OF THE INVENTION

The present invention relates to compounds useful as fragrance or flavor components in fragrance or flavor compositions.

BACKGROUND OF THE INVENTION

The fragrance industry is constantly reliant on the development of new chemicals with favorable organoleptic properties to provide perfumers and other persons the capability of creating new, unique fragrances for applications such as personal care products, air care products, perfumes, colognes and the like.

3-methoxy-3-methyl-1-butanol, also known as Solfit™, is known in the perfume industry and has been applied in many consumer products (WO 9512379; JP 2001226246; JP 2005290236; JP 001104462). The structure of 3-methoxy-3-methyl-1-butanol is shown below:

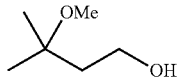

Some esters derived from this alcohol have been employed as solvents for consumer products (EP 462605A2). Ether analogues of this alcohol have been used as intermediates to useful homoallylic alcohol entities (U.S. Pat. No. 4,990,697).

SUMMARY OF THE INVENTION

The present invention is directed to the synthesis and application of 3-methoxy-3-methyl-1-butanol derivatives having unique and desired odor or organoleptic characteristics. The compounds of the present invention can be employed alone or incorporated as perfumery ingredients to enhance already existing fragrance compositions, solvents, media and the like.

In one embodiment, the present invention provides fragrance compounds of the formula (I),

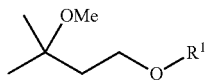

wherein $R^1$ is an unsubstituted or substituted $C_{1-6}$ straight chain alkyl, an unsubstituted or substituted $C_{3-6}$ branched chain alkyl, an unsubstituted or substituted $C_{3-6}$ straight chain alkenyl, an unsubstituted or substituted $C_{3-6}$ branched chain alkenyl, an unsubstituted or substituted $C_{3-6}$ cycloalkyl, an unsubstituted or substituted $C_{1-6}$ alkoxy, nitrile, halo, an unsubstituted or substituted phenyl, an unsubstituted or substituted benzyl, an unsubstituted or substituted naphthyl, an unsubstituted or substituted aryl, an unsubstituted or substituted piperazino, an unsubstituted or substituted morpholinyl, amino, an unsubstituted or substituted $C_{1-6}$ alkylamino, an unsubstituted or substituted $C_{6-12}$ arylamino, an unsubstituted or substituted $C_{1-6}$ dialkylamino, an unsubstituted or substituted $C_{6-12}$ diarylamino, carboxy-$C_{1-6}$ alkylamino, carboxy-$C_{1-6}$ dialkylamino, an unsubstituted or substituted acetoxy, carboxy, an unsubstituted or substituted carboxyethyl, an unsubstituted or substituted $C_{1-6}$ alkylcarbonyl, thio, an unsubstituted or substituted $C_{1-6}$ alkylthio, an unsubstituted or substituted $C_{1-6}$ alkyloxy, carboxamido, an unsubstituted or substituted $C_{1-6}$ alkylcarboxamido, an unsubstituted or substituted $C_{1-6}$ dialkylcarboxamido, an unsubstituted or substituted phenoxy, an unsubstituted or substituted benzyloxy, phenylcarbonyl, benzylcarbonyl, an unsubstituted or substituted nitrophenyl, $C_{1-6}$ trialkylsilyl or nitro, an unsubstituted or substituted $C_{1-12}$ straight chain alkyl sulfonate, an unsubstituted or substituted $C_{1-12}$ branched chain alkyl sulfonate, an unsubstituted or substituted $C_{1-12}$ straight chain alkenyl sulfonate, an unsubstituted or substituted $C_{1-12}$ branched chain alkenyl sulfonate, an unsubstituted or substituted $C_{1-12}$ straight chain aryl sulfonate or an unsubstituted or substituted $C_{1-12}$ branched chain aryl sulfonate.

In a preferred embodiment, $R^1$ as shown in formula I above, is an unsubstituted or substituted $C_{1-6}$ straight chain alkyl, an unsubstituted or substituted $C_{3-6}$ branched chain alkyl, an unsubstituted or substituted $C_{3-6}$ straight chain alkenyl, an unsubstituted or substituted $C_{3-6}$ branched chain alkenyl, an unsubstituted or substituted $C_{3-6}$ cycloalkyl, an unsubstituted or substituted $C_{1-6}$ alkoxy, nitrile, halo, amino, an unsubstituted or substituted $C_{1-6}$ alkylamino, an unsubstituted or substituted $C_{1-6}$ dialkylamino, carboxy-$C_{1-6}$ alkylamino, carboxy-$C_{1-6}$ dialkylamino, an unsubstituted or substituted acetoxy, carboxy, an unsubstituted or substituted carboxyethyl, an unsubstituted or substituted $C_{1-6}$ alkylcarbonyl, an unsubstituted or substituted $C_{1-6}$ alkylcarboxy, an unsubstituted or substituted $C_{1-6}$ alkylthio, an unsubstituted or substituted $C_{1-6}$ alkyloxy, carboxamido, an unsubstituted or substituted $C_{1-6}$ alkylcarboxamido or an unsubstituted or substituted $C_{1-6}$ dialkylcarboxamido.

In a more preferred embodiment, $R^1$ is a $C_{1-6}$ straight chain alkyl, $C_{3-6}$ branched chain alkyl, an unsubstituted or substituted $C_{1-6}$ alkenyl, an unsubstituted or substituted $C_{1-6}$ acyl, or aryl.

In another embodiment, the invention provides fragrance compounds of the formula (II),

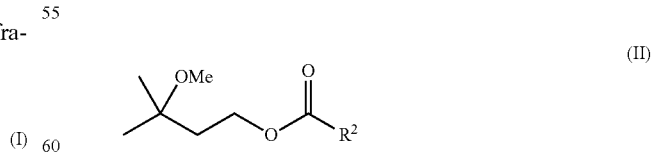

wherein $R^2$ is the same as described for $R^1$ above in paragraph 6. In an alternative embodiment, $R^2$ is as $R^1$ is described above in paragraphs 7 or 8. Additionally, $R^2$ may be hydrogen. Usually, the alkyl 3-methoxy-3-methyl-1-butanol esters represented by formula II have a strong fruity note associated with them.

In another embodiment, the invention provides fragrance compounds of the formula (III),

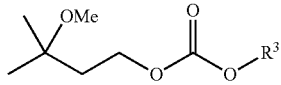
(III)

wherein $R^3$ is the same as described for $R^2$ above. Generally, the carbonate compounds represented by formula III have weak, varying odor characteristics but maintain a light and soft quality.

In another embodiment, the invention provides fragrance compounds of the formula (IV),

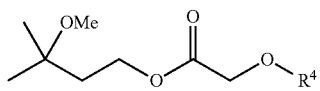
(IV)

wherein $R^4$ is the same as described for $R^2$ above. For example, when the alcohol, 3-methoxy-3-methyl-1-butanol, is reacted with an alkoxy acetic acid, a compound of formula (IV) will result from the condensation reaction. Glycolates represented by formula IV generally have a consistent light, powdery musk property.

In another embodiment, the invention provides fragrance compounds of the formula (V),

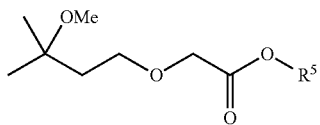
(V)

wherein $R^5$ is the same as described for $R^2$ above. Compounds encompassed by formula (V) often possess variations of plastic and green olfactory notes.

In another embodiment, the invention provides fragrance compounds of the formula (VI),

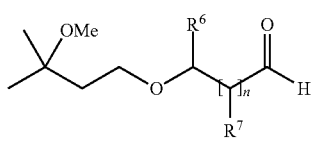
(VI)

wherein $R^6$ and/or $R^7$ is a hydrogen or an unsubstituted or substituted $C_{1-6}$ straight chain alkyl, an unsubstituted or substituted $C_{3-6}$ branched chain alkyl group and n=0-1. Preferably, $R^6$ and/or $R^7$ are hydrogen or a methyl group.

Preferred fragrance compounds are set forth in the table below, in which $R_n$ refers to the R group of the respective formula.

TABLE 1

| Compound No. | Formula | $R_n$ | Olfactory Description |
|---|---|---|---|
| 1 | I | —$CH_2CH(OCH_3)_2$ | weak, marine-like, clean |
| 2 | I | —$CH_2CH$=$CH_2$ | citrus, herbal, pine, sweet orange, candy |
| 3 | I | —$CH_2C(CH_3)$=$CH_2$ | citrus, green, lemon, slight orange |
| 4 | I | —$CH_2CH$=$C(CH_3)_2$ | green, chocolate, sweet, bitter |
| 5 | I | —$CH(CH_3)CH$=$CH_2$ | strong, mint, citrus, rose |
| 6 | I | —$CH_2CH_2CH_3$ | woody, floral, slightly bitter banana |
| 7 | I | —$CH_2CH(CH_3)_2$ | woody, green pear, slight chocolate |
| 8 | I | —$CH_2CH_2CH(CH_3)_2$ | chocolate, liqueur, sour, slightly pungent |
| 9 | I | —$CH_2CH_2C(OCH_3)(CH_3)_2$ | mold, mildew |
| 10 | II | —H | woody, camphoraceous, dry, chemical |
| 11 | II | —$CH_2CH_3$ | fruity, banana, floral, bubble gum |
| 12 | II | —$CH(CH_3)_2$ | fruity, green, pear, apple, sour |
| 13 | II | —$C(CH_3)$=$CHCH_3$ | sugary, sweet sap, green |
| 14 | III | —$CH_3$ | weak, light, green, floral |
| 15 | III | —$CH_2CH$=$CH_2$ | weak, soft chocolate, airy |
| 16 | III | —$CH_2CH_2CH_3$ | weak, soft musk, light vanilla |
| 17 | IV | —$CH_3$ | weak, fruity, slight coconut, powder musk |
| 18 | IV | —$CH_2CH_3$ | powder musk, fresh, soft, light, clean |
| 19 | IV | —$CH(CH_3)_2$ | very weak, powder musk |
| 20 | V | —$CH_3$ | metallic green, plastic |
| 21 | V | —$CH_2CH_3$ | vegetable green, spicy, plastic |
| 22 | V | —$CH(CH_3)_2$ | green, licorice, slightly mint, fresh |
| 23 | VI | —H ($R^6$) (n = 0) | fresh, melon, clean, floral, muguet, green |
| 24 | VI | —$CH_3$ ($R^6$) (n = 0) | fresh, watery melon, clean, floral, muguet |
| 25 | VI | —H ($R^6$), —H ($R^7$) (n = 1) | waxy, oily, muguet, light floral |
| 26 | VI | —$CH_3$ ($R^6$) —H ($R^7$) (n = 1) | waxy, oily, fatty |

In one embodiment the fragrance compound is selected from 3-methoxy-3-methylbutyl 2-ethoxyacetate, 2-(3-methoxy-3-methylbutoxy)ethanal, 1-methoxy-1,1-dimethyl-3-(3-methylbut-2-enyloxy)propane, 1-methoxy-1,1-dimethyl-3-prop-2-enyloxypropane, and 1-methoxy-1,1-dimethyl-3-(1-methylprop-2-enyloxy)propane.

In one aspect, the present invention provides a method to modify, enhance or improve olfactory and/or organoleptic property (e.g odor or flavor property) of a fragrance or flavor composition by adding to said composition an olfactory or organoleptic effective quantity of the compound of formulas (I-VI). In one embodiment, a fragrance compound is added to a fragrance carrier, fragrance base or both to provide a fragrance composition. In an alternative embodiment, a flavor compound is added to a flavor carrier to provide a flavor composition. It is understood here also that the invention may be described as the use of any composition containing formulas (I-VI) in fragrance and/or flavor compositions.

DETAILED DESCRIPTION OF THE INVENTION

Fragrance Compositions

The present invention is directed to the use of the above compounds as fragrances in a fragrance composition. The compounds can be incorporated alone, as a mixture of two or more of said compounds, or as an enhancer to an existing fragrance composition (discussed below). These compounds add a favorable olfactory effect to the desired product. The compounds are typically present in an amount of from about 0.001 to about 30.0 by weight of the total fragrance composition. Typically a more preferred embodiment would contain between 0.01% and 20% by weight and a most preferred embodiment would contain between 0.01% and 10% by weight. None of these examples shown are meant to be limiting or restrictive on the use of the material as stated.

One embodiment of the present inventions provides a method to modify, enhance or improve the odor properties of a fragrance composition by adding to said composition an olfactory effective quantity of the compound of formulas (I-VI). The invention may also be described as the use of any composition containing compound (I-VI) which can be advantageously employed in the fragrance industry as active ingredients.

Such compositions may contain or consist of at least one ingredient selected from a group consisting of a fragrance carrier and a fragrance base. Such compositions may also consist of at least one fragrance adjuvant.

Said fragrance carriers may be a liquid or a solid and typically do not significantly alter the olfactory properties of the fragrance ingredients. Some non-limiting examples of fragrance carriers include an emulsifying system, encapsulating materials, natural or modified starches, polymers, gums, pectins, gelatinous or porous cellular materials, waxes, and solvents which are typically employed in fragrance applications.

Said fragrance base refers to any composition comprising at least one fragrance co-ingredient. In general, these co-ingredients belong to chemical classes such as, but not limited to: alcohols, aldehydes, ketones, esters, ethers, acetals, oximes, acetates, nitriles, terpenes, saturated and unsaturated hydrocarbons and essential oils of natural or synthetic origins.

Table 2 provides an example of a formulated fragrance in which compounds of the present invention can be added.

TABLE 2

Fragrance Formulation (ingredients are listed in parts per formulation based on a total of 1000 parts by weight, and also shown as WT % by formula amount) %

| MATERIAL | Parts/1000 | Wt % |
| --- | --- | --- |
| Acetyl Tetralin | 20 | 2.0 |
| Ambretone | 5 | 0.5 |
| Benzy Acetate | 100 | 10.0 |
| Bergamot Synth | 25 | 2.5 |
| Citral Synth @ 10% | 10 | 1.0 |
| Citronellol, Laevo | 40 | 4.0 |
| Citronellyl Acetate, Laevo | 5 | 0.5 |
| Citronellyl Nitrile, Laevo | 7 | 0.7 |
| Cyclacet | 45 | 4.5 |
| Trepanol | 15 | 1.5 |
| DH Myrcenol | 125 | 12.5 |
| Dynascone @ 10% | 5 | 0.5 |
| Eugenol | 5 | 0.5 |
| Geranium Oil | 10 | 1.0 |
| Hedione | 27 | 2.7 |

TABLE 2-continued

Fragrance Formulation (ingredients are listed in parts per formulation based on a total of 1000 parts by weight, and also shown as WT % by formula amount) %

| MATERIAL | Parts/1000 | Wt % |
| --- | --- | --- |
| Heliotropine | 8 | 0.8 |
| Hindinol | 5 | 0.5 |
| Ionone, Beta | 25 | 2.5 |
| Iso Bornyl Methyl Ether | 25 | 2.5 |
| Iso E Super | 25 | 2.5 |
| Iso Propxy Ethyl Salicylate | 10 | 1.0 |
| Linalool Syn | 85 | 8.5 |
| Linalyl Acetate | 15 | 1.5 |
| Melonal @10% | 5 | 0.5 |
| Methyl Ionone, Gamma | 55 | 5.5 |
| Norlimbanol Dextro @ 10% | 6 | 0.6 |
| Orange Oil Brazilian | 25 | 2.5 |
| Phenyl Ethyl Alcohol | 30 | 3.0 |
| Rose Oxide | 3 | 0.3 |
| Styrallyl Acetate | 8 | 0.8 |
| Tamarine Base 41.310 G | 3 | 0.3 |
| Terpineol | 20 | 2.0 |
| Thesaron | 7 | 0.7 |
| Triplal Extra | 3 | 0.3 |
| Undecalactone, Gamma | 20 | 2.0 |
| Vanillin | 5 | 0.5 |
| Vertenex | 85 | 8.5 |
| Ylang Oil Extra | 3 | 0.3 |
| 2-(3-methoxy-3-methylbutoxy)ethanal [Compound 23; TABLE 1] | 80 | 8.0 |

As used herein, olfactory effective quantity will be defined as the amount of said compound in a fragrance composition in which the individual component will contribute its characteristic olfactory properties, for example an olfactory property found to be more hedonistically appealing. A person of ordinary skill in the art may optimize the olfactory effect of the fragrance composition based on the incorporation of a fragrance compound of the present invention. The fragrance compounds may be used individually, or a part of mixture such that the sum of the effects of all fragrance ingredients present in the mixture yields a higher hedonistic rating. Therefore, the compounds embodied in the present invention can be employed to modify the characteristics of existing fragrance composition via their own olfactory properties or through additively effecting the contributions of other ingredient(s) present within the said composition. The quantity will vary widely depending on the other ingredients present, their relative amounts, the desired effect and the nature of the product.

Flavor Composition

Compounds of formulas (I-VI) can be employed alone or incorporated into mixtures to enhance already existing flavor compositions. These compounds add a favorable organoleptic property and effect to the desired product. The compounds are typically present in an amount of from about 0.01% to about 20.0% by weight of the total flavor composition. Typically a more preferred embodiment would contain between 0.01% and 10% by weight and a most preferred embodiment would contain between 0.01% and 5% by weight. None of these examples shown are meant to be limiting or restrictive on the use of the material as stated.

As used herein, organoleptic effective quantity will be defined as the amount of said compound in a flavor composition in which the individual component will contribute its characteristic flavor properties. However, the organoleptic effect of the flavor composition will be the sum of the effects of all flavor ingredients present. Therefore, the compounds embodied in the present invention can be employed to modify the characteristics of the flavor composition via their own organoleptic properties or through additively effecting the contributions of other ingredient(s) present within the said composition. The quantity will vary widely depending on the presence of other ingredients present, their relative amounts, the desired effect and the nature of the product.

The flavor carrier may be a liquid or a solid and typically do not significantly alter the olfactory or organoleptic properties of the flavor ingredients, respectively. Some non-limiting examples of flavor carriers include an emulsifying system, encapsulating materials, natural or modified starches, polymers, pectins, proteins, polysaccharides, gums and solvents which are typically employed in flavor applications.

As used herein, the term "flavor carrier" may also encompass the food or beverage to which the fragrance compound (i.e. compounds encompassed by formulas I-VI) are added. Examples of such foods or beverages include, but are not limited to carbonated fruit beverages, carbonated cola drinks, wine coolers, cordials, flavored water, powders for drinks (e.g., powdered sports or "hydrating" drinks), hard candy, soft candy, taffy, chocolates, sugarless candies, chewing gum, bubble gum, condiments, spices and seasonings, dry cereal, oatmeal, granola bars, soups, alcoholic beverages, energy beverages, juices, teas, coffees, salsa, gel beads, film strips for halitosis, gelatin candies, pectin candies, starch candies, lozenges, cough drops, throat lozenges, throat sprays, toothpastes and mouth rinses.

Intended Use

Compounds of formulas (I-VI) can be employed alone or incorporated into mixtures to enhance already existing fragrance compositions, solvents, media and the like. The use of such compounds is applicable to a wide variety of products in the perfume industry for consumer use such as, but not limited to: sprays, candles, air fresheners, perfumes, colognes, gels, soft solids, solids, devices for introducing said compounds into a space (e.g., a plug-in electrical device or a battery operated device), a liquid wicking system, personal care products such as soaps, talcum powder, antiperspirants, personal wash bar, personal wash liquid, personal wipe, deodorants, shampoos, conditioners, styling sprays, mousses, hair wipes, hair sprays, hair pomades, shower gels and shaving lotions; cosmetics such as oils, lotions and ointments; as well as detergents (e.g., synthetic detergent), fabric care products (e.g., fabric washing liquids and powders, fabric softeners, fabric conditioners), wipes, dishwashing liquids and powders, and household cleaning agents (e.g., hard surface cleaning liquids and powders and aqueous and non-aqueous sprays). The sprays can be aqueous or non-aqueous. The candles and gels can be opaque, translucent, or transparent, and may contain optional ingredients to enhance their appearance. The plug-in and battery-operated devices can include devices that vaporize the fragrance by heat, evaporation, or nebulization.

The use of such compounds is also applicable to a wide variety of products in the flavor industry such as, but not limited to: foodstuffs such as baked goods, dairy products, desserts, etc.; beverages such as juices, sodas, flavored waters, etc.; confectionaries such as sweets, hard candy, gums, gelatinous materials, etc. The flavor compositions can also be added to pharmaceutical applications, such as lozenges, strips to deliver medicines or personal care products (e.g. fresh breath strips), cough syrup or other liquid or bucally administered medicines.

Synthesis Details

Compounds of formula I may be isolated from the reaction of 3-methoxy-3-methyl-1-butoxide with an alkyl halide. Similarly, reaction of this alkoxide with an allyl halide results in a compound of formula (I) as well. Table 1 lists the olfactory properties of various novel compounds synthesized in accordance to formula (I). In particular, the unsaturated 3-methoxy-3-methyl-1-butanol ether derivatives described in the present invention all contain citrus and/or green notes incorporated into their odor compositions. Saturation of these olefinic substituents via hydrogenation results in a woody, fruitier olfactory character.

Compounds encompassed by formula II can be synthesized via simple condensation reactions between the alcohol, 3-methoxy-3-methyl-1-butanol, and the respective carboxylic acid. Alternatively, compounds of formula (II) can be synthesized by direct reaction of the alcohol with the respective acid chloride. Table 1 lists the odor characteristics of various novel compounds synthesized in accordance to formula (II).

The syntheses of all compounds related to formula (II) proceed with high yields. As represented in Table 1, the majority of the alkyl 3-methoxy-3-methyl-1-butanol esters have a strong fruity note associated with them.

Compounds of formula III may be isolated from the reaction of 3-methoxy-3-methyl-1-butanol (Solfit™) with an alkyl chloroformate. The synthesis proceeds in a straight forward, facile manner. Table 1 lists the olfactory properties of various novel compounds synthesized in accordance to formula (III). The fragrance compounds encompassed by formula III generally maintain a light and soft quality.

The syntheses of compounds (glycolates) encompassed by formula (IV) proceeded smoothly and in high yield. Simple esterification of various alkoxy carboxylic acids with 3-methoxy-3-methyl-1-butanol in the presence of a catalytic amount of acid resulted in the desired products. Glycolates of this nature have a consistent light, powdery musk property. The musk qualities associated with these chemical entities have been reported in other glycolate-type compounds (See, e.g., U.S. Published Application No. 2006/0052277, which is hereby incorporated by reference).

The present inventors have found that glycolates encompassed by formula (V) can be isolated in high yields when the reaction specifically employs 2-(3-methoxy-3-methylbutoxy)acetic acid with a respective alcohol to undergo esterification in similar fashion to the syntheses of compounds of formula (IV). Alternatively, reactions involving an alkyl halo-acetate with 3-methoxy-3-methyl-1-butoxide result in a low yield of the desired glycolate due to a mixture of undesired side products.

The synthesis of the compound of formula (VI) in which n=0 and $R^6$=hydrogen proceeded smoothly via its dimethyl acetal precursor. Cleavage of the acetal group under acidic conditions afforded the respective acetaldehyde. This compound can also be synthesized via ozonolysis of allyl 3-methoxy-3-methyl-1-butanol ether. Such an approach was taken for the compound of formula (VI) in which n=0 and $R^6$=methyl. Both compounds possess odor characteristics which can be described as clean, melon-like and fresh with very strong diffusive properties.

The synthesis of compounds of formula (VI) in which n=1 and $R^6$=hydrogen or a methyl group was based on a revised adaptation of previously reported syntheses between alcohols and α-β-unsaturated aldehydes (U.S. Pat. No. 2,694,733; Feldman, D. P.; Stonkus, V. V.; Shimanskaya, M. V.; Avots, A. A. Russ. J. Gen. Chem. 1995, 65, 250-253). In the present case, acrolein and crotonaldehyde have been chosen as the α-β-unsaturated aldehydes. In each of the previously reported syntheses for reactions of this type, specific conditions involving the buffer capacity of the system were stressed. The syntheses reported here proceeded with extremely low yields (<5%) when employing such conditions. The present inventors found that the presence of a catalytic amount of acid greatly promotes the formation of the desired aldehydes. As listed in Table 1, such aldehydes of this nature have a much more waxy, fatty-type aroma than the acetaldehyde analogues (n=0).

Example 1

This example illustrates the synthesis of 3-(2,2-dimethoxyethoxy)-1-methoxy-1,1-dimethylpropane.

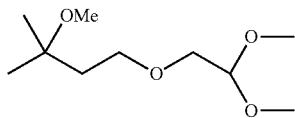

A suspension of sodium hydride (11.8 g, 0.47 mol) in anhydrous THF (400 mL) was warmed to approximately 40° C. under an inert atmosphere. A portion of 3-methoxy-3-methyl-1-butanol (50.0 g, 0.42 mol) was then added dropwise via syringe over a period of 20 minutes during which time the temperature of the mixture was slowly raised to 70° C. at 5 degree intervals. After one hour, bromoacetaldehyde dimethyl acetal (54.0 mL, 0.46 mol) was added dropwise via syringe over a period of 30 minutes and the mixture was stirred vigorously at 70° C. for 16 hours. After this time, the mixture was cooled to room temperature, treated with $H_2O$ (200 mL) and extracted with diethyl ether (3×200 mL). The organic phases were collected and washed with saturated $NaHCO_3$ (aq.) (2×200 mL) followed by $H_2O$ (2×100 mL). The organic phase was dried with $MgSO_4$ and the solvent was removed under reduced pressure. The resulting light yellow liquid was fractionally distilled (87° C., 3.00 torr) to yield the desired colorless, pure ether (57.0 g, 65.5%). Odor: weak, marine-like, clean. GC/MS(EI): m/z (%)—206(1), 191(1), 159(1), 143(3), 127(4), 111(5), 97(3), 89(2), 85(13), 75(100), 73(37), 69(8), 58(4), 55(3), 47(8), 45(15), 43(7). $^1H$ NMR ($CDCl_3$); δ 1.16 (s, 6H), 1.81 (t, J=7.33 Hz, 2H), 3.17 (s, 3H), 3.38 (s, 6H), 3.47 (d, J=5.04 Hz, 2H), 3.55 (t, J=7.33 Hz, 2H), 4.48 (t, J=5.04 Hz, 1H). $^{13}C$ NMR ($CDCl_3$): δ 25.4, 39.3, 49.2, 53.9, 68.0, 70.8, 73.7, 102.9.

Example 2

This example illustrates the synthesis of 1-methoxy-1,1-dimethyl-3-prop-2-enyloxypropane.

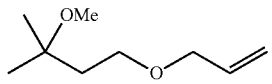

This compound was synthesized employing a procedure analogous to Example 1 using 3-methoxy-3-methyl-1-butanol (25.0 g, 0.21 mol) and allyl chloride (16.4 mL, 0.20 mol). The isolated crude material was fractionally distilled (22° C., 0.80 torr) resulting in a colorless, pure liquid (22.5 g, 70.8%). Odor: citrus, herbal, pine, sweet orange, candy. GC/MS(EI): m/z (%)—158(1), 143(2), 126(1), 111(3), 97(1), 87(9), 85(7), 73(100), 71(14), 57(9), 55(9), 45(7), 43(13), 41(25). $^1H$ NMR ($CDCl_3$): δ 1.16 (s, 6H), 1.80 (t, J=7.33 Hz, 2H), 3.17 (s, 3H), 3.50 (t, J=7.79 Hz, 2H), 3.96 (d, J=5.96 Hz, 2H), 5.15 (dd, J=11.9 Hz, 1H), 5.25 (dd, J=18.8 Hz, 1H), 5.90 (m, 1H). $^{13}C$ NMR ($CDCl_3$): δ 25.4, 39.3, 49.2, 66.7, 71.9, 73.8, 116.8, 135.1.

Example 3

This example illustrates the synthesis of 1-methoxy-1,1-dimethyl-3-(2-methylprop-2-enyloxy)propane.

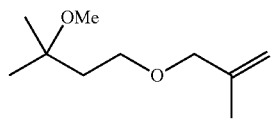

This compound was synthesized employing a procedure analogous to Example 1 using 3-methoxy-3-methyl-1-butanol (25.0 g, 0.21 mol) and methallyl chloride (20.7 mL, 0.21 mol). The isolated crude material was fractionally distilled (103° C., 36.0 torr) resulting in a colorless, pure liquid (28.8 g, 79.3%). Odor: citrus, green, lemon, slight orange. GC/MS (EI): m/z (%)—172(1), 157(1), 140(1), 125(9), 111(2), 101 (2), 95(7), 87(9), 85(10), 73(100), 71(11), 69(14), 55(36), 45(9), 43(12), 41(10). $^1H$ NMR ($CDCl_3$): δ 1.17 (s, 6H), 1.72 (s, 3H), 1.81 (t, J=6.87 Hz, 2H), 3.18 (s, 3H), 3.47 (t, 0.1=7.33 Hz, 2H), 3.85 (s, 2H), 4.87 (s, 1H), 4.94 (s, 1H). $^{13}C$ NMR ($CDCl_3$): δ 19.5, 25.5, 39.4, 49.2, 66.5, 73.8, 75.0, 111.8, 142.6.

Example 4

This example illustrates the synthesis of 1-methoxy-1,1-dimethyl-3-(3-methylbut-2-enyloxy)propane.

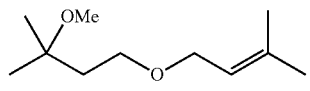

This compound was synthesized employing a procedure analogous to Example 1 using 3-methoxy-3-methyl-1-butanol (25.0 g, 0.21 mol) and prenyl chloride (23.9 mL, 0.21 mol). The isolated crude material was fractionally distilled (66° C., 3.00 torr) resulting in a colorless, pure liquid (30.4 g, 77.0%). Odor: green, chocolate, sweet, bitter. GC/MS (EI): m/z (%)—186(1), 171(1), 154(1), 139(58), 103(4), 85(44), 78(4), 73(100), 69(86), 55(11), 45(12), 43(12), 41(26). $^1H$ NMR ($CDCl_3$): δ 1.15 (s, 6H), 1.66 (s, 3H), 1.73 (s, 3H), 1.79 (t, J=7.33 Hz, 2H), 3.17 (s, 3H), 3.48 (t, J=7.33 Hz, 2H), 3.93 (d, J=6.87 Hz, 2H), 5.34 (t, J=7.33 Hz, 1H). $^{13}C$ NMR ($CDCl_3$): δ 18.1, 25.5, 25.9, 39.2, 49.2, 66.5, 67.5, 73.8, 121.2, 136.8.

Example 5

This example illustrates the synthesis of 1-methoxy-1,1-dimethyl-3-propoxypropane.

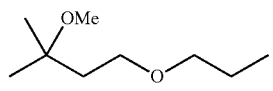

A portion of the unsaturated ether, 1-methoxy-1,1-dimethyl-3-prop-2-enyloxypropane, (20.0 g, 0.13 mol) was dissolved in absolute EtOH (120 mL) and to this was added 5% (w/w) catalyst (5% Pd—C). The suspension was stirred at ambient temperature and treated with H$_2$ (250 psi) for 16 hours. Upon completion, the suspension was filtered through a glass frit (M) filter packed with filter paper and celite and rinsed with ethyl acetate. The solvent was removed under reduced pressure via rotary evaporation affording a light yellow liquid which was fractionally distilled (58° C., 9.70 torr) to yield the desired colorless, pure ether (11.9 g, 59.1%). Odor: woody, floral, slightly bitter banana. GC/MS (EI): m/z (%)—160(1), 145(2), 128(8), 113(12), 87(8), 73(100), 71(20), 55(7), 43(24), 41(11). $^1$H NMR (CDCl$_3$): δ 0.90 (t, J=7.33 Hz, 3H), 1.16 (s, 6H), 1.58 (m, 2H), 1.78 (t, J=7.33 Hz, 2H), 3.17 (s, 3H), 3.35 (t, J=6.42 Hz, 2H), 3.47 (t, J=7.79 Hz, 2H). $^{13}$C NMR (CDCl$_3$): δ 10.7, 23.0, 25.5, 39.2, 49.2, 67.0, 72.8, 73.9.

Example 6

This example illustrates the synthesis of 1-methoxy-1,1-dimethyl-3-(2-methylpropoxyl)propane.

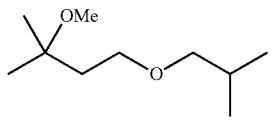

This compound was synthesized employing a procedure analogous to Example 5 using 1-methoxy-1,1-dimethyl-3-(2-methylprop-2-enyloxy)propane (20.0 g, 0.12 mol). The isolated crude material was fractionally distilled (53° C., 5.00 torr) resulting in a colorless, pure liquid (16.0 g, 80.0%). Odor: woody, green pear, slight chocolate. GC/MS (EI): m/z (%)—174(1), 159(1), 142(5), 127(3), 99(2), 87(9), 85(5), 73(100), 71(17), 57(26), 43(11), 41(14). $^1$H NMR (CDCl$_3$): δ 0.88 (d, J=6.87 Hz, 6H), 1.16 (s, 6H), 1.78 (t, J=7.33 Hz, 2H), 1.83 (m, 1H), 3.15 (d, J=6.42 Hz, 2H), 3.18 (s, 3H), 3.47 (J=7.33 Hz, 2H). $^{13}$C NMR (CDCl$_3$): δ 19.5, 25.5, 28.5, 39.2, 49.2, 67.2, 73.9, 78.1.

Example 7

This example illustrates the synthesis of 1-methoxy-1,1-dimethyl-3-(3-methylbutoxyl)propane.

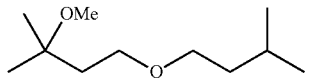

This compound was synthesized employing a procedure analogous to Example 5 using 1-methoxy-1,1-dimethyl-3-(3-methylbut-2-enyloxy)propane (20.0 g, 0.11 mol). The isolated crude material was distilled via Kugelrohr apparatus (25° C., 0.15 torr) resulting in a colorless, pure liquid (9.93 g, 49.2%). Odor: chocolate, liqueur, sour, slightly pungent. GC/MS(EI): m/z (%)—188(1), 173(1), 156(4), 141(11), 99(7), 87(11), 73(100), 71(38), 55(11), 43(30), 41(14). $^1$H NMR (CDCl$_3$): δ 0.89 (d, J=6.87 Hz, 6H), 1.16 (s, 6H), 1.45 (q, J=6.87 Hz, 2H), 1.67 (m, 1H), 1.78 (t, J=7.33 Hz, 2H), 3.18 (s, 3H), 3.41 (t, J=6.87 Hz, 2H), 3.47 (t, J=7.33 Hz, 2H). $^{13}$C NMR (CDCl$_3$): δ 22.7, 25.2, 25.5, 38.7, 39.2, 49.2, 67.1, 69.5, 73.9.

Example 8

This example illustrates the synthesis of 3-methoxy-3-methylbutyl formate.

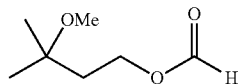

A portion of 3-methoxy-3-methyl-1-butanol (30.0 g, 0.25 mol) was dissolved in neat formic acid (60.9 g, 1.27 mol) and was stirred at ambient temperature for approximately 6 hours. Upon completion (monitored via GC), H$_2$O (100 mL) was added and the solution was extracted with diethyl ether (3×75 mL). The organic phases were collected and washed with saturated NaHCO$_3$ (aq.) (3×100 mL) followed by H$_2$O (2×50 mL). The organic phase was dried with MgSO$_4$ and the solvent was removed under reduced pressure. The resulting light yellow liquid was fractionally distilled (57° C., 9.00 torr) to yield the desired colorless, pure product (20.9 g, 56.3%). Odor: woody, camphoraceous, dry, chemical. GC/MS(EI): m/z (%)—146(1), 131(1), 85(43), 73(100), 69(14), 55(15), 43(12), 41(13). $^1$H NMR (CDCl$_3$): δ 1.18 (s, 6H), 1.85 (t, J=7.33 Hz, 2H), 3.18 (s, 3H), 4.27 (t, J=7.33 Hz, 2H), 8.03 (s, 1H). $^{13}$C NMR (CDCl$_3$): δ 25.2, 38.3, 49.3, 60.7, 73.5, 161.3.

Example 9

This example illustrates the synthesis of 3-methoxy-3-methylbutyl propanoate.

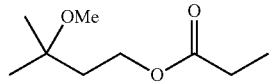

A portion of 3-methoxy-3-methyl-1-butanol (25.0 g, 0.21 mol) was dissolved in anhydrous THF (200 mL) and purged with nitrogen. To this solution was added the propionyl chloride (20.2 mL, 0.23 mol) dropwise over a 15-minute period. The solution was stirred at ambient temperatures for 2 hours. Upon completion (monitored via GC), H$_2$O (100 mL) was added and the solution was extracted with diethyl ether (3×75 mL). The organic phases were collected and washed with saturated NaHCO$_3$ (aq.) (3×100 mL) followed by H$_2$O (2×50 mL). The organic phase was dried with MgSO$_4$ and the solvent was removed under reduced pressure. The resulting yellow liquid was fractionally distilled (110° C., 36.0 torr) to yield the desired colorless, pure product (29.4 g, 80.1%). Odor: fruity, banana, floral, bubble gum. GC/MS(EI): m/z (%)—173(1), 159(1), 143(1), 101(1), 85(57), 73(100), 69(27), 57(24), 55(16), 43(10), 41(10). $^1$H NMR (CDCl$_3$): δ 1.12 (t, J=7.33 Hz, 3H), 1.17 (s, 6H), 1.81 (t, J=7.33 Hz, 2H), 2.30 (t, J=7.33 Hz, 2H), 3.18 (s, 3H), 4.15 (t, J=7.33 Hz, 2H). $^{13}$C NMR (CDCl$_3$): δ 9.2, 25.3, 27.7, 38.3, 49.3, 61.0, 73.6, 174.6.

Example 10

This example illustrates the synthesis of 3-methoxy-3-methylbutyl 2-methylpropanoate.

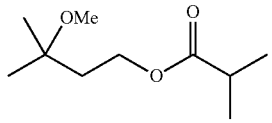

This compound was synthesized employing a procedure analogous to Example 9 using 3-methoxy-3-methyl-1-butanol (25.0 g, 0.21 mol) and isobutyryl chloride (24.4 mL, 0.23 mol). The isolated crude material was fractionally distilled (58° C., 3.00 torr) resulting in a colorless, pure liquid (29.6 g, 74.2%). Odor: fruity, green, pear, apple, sour. GC/MS(EI): m/z (%)—188(1), 173(1), 157(1), 115(1), 101(1), 85(55), 73(100), 71(12), 69(25), 55(13), 43(26), 41(15). $^1$H NMR (CDCl$_3$): δ 1.14 (d, J=7.33 Hz, 6H), 1.18 (s, 6H), 1.81 (t, J=7.33 Hz, 2H), 2.51 (m, 1H), 3.18 (s, 3H), 4.15 (t, J=7.33 Hz, 2H). $^{13}$C NMR (CDCl$_3$): δ 19.0, 25.3, 34.1, 38.3, 49.3, 61.0, 73.6, 177.3.

Example 11

This example illustrates the synthesis of 3-methoxy-3-methylbutyl (2E)-2-methylbut-2-enoate.

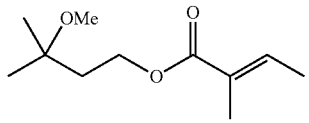

Portions of tiglic acid (12.6 g, 0.13 mol) and p-toluene sulfonic acid (1.21 g, 6.35 mmol) were dissolved in 3-methoxy-3-methyl-1-butanol (45.0 g, 0.38 mol) and stirred vigorously while heated at 40° C. for 27 hours. After this time, the solution was cooled to room temperature and diethyl ether was added (100 mL). The solution was washed with saturated NaHCO$_3$ (3×75 mL) followed by H$_2$O (100 mL). The aqueous fractions were back-extracted with diethyl ether (50 mL) and the organic layers were dried with MgSO$_4$. The solvent removed via rotary evaporation and the resulting clear liquid was fractionally distilled (76° C., 1.23 torr) to afford the desired colorless, pure ester (5.25 g, 20.8%). Odor: sugary, sweet sap, green. GC/MS(EI): m/z (%)—200(1), 185(1), 169(1), 127(1), 101(6), 85(50), 73(100), 69(16), 55(26), 43(7), 41(8). $^1$H NMR (CDCl$_3$): δ 1.18 (s, 6H), 1.76 (d, J=7.79 Hz, 3H), 1.81 (s, 3H), 1.85 (t, J=7.33 Hz, 2H), 3.19 (s, 3H), 4.21 (t, J=7.33 Hz, 2H), 6.83 (dq, J=8.71 Hz, 1H). $^{13}$C NMR (CDCl$_3$): δ 12.1, 14.4, 25.4, 38.3, 49.3, 61.1, 73.6, 128.8, 137.0, 168.3.

Example 12

This example illustrates the synthesis of 3-methoxy-3-methylbutyl methoxyformate.

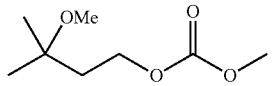

A portion of 3-methoxy-3-methyl-1-butanol (30.0 g, 0.25 mol) was dissolved in anhydrous THF (100 mL) and purged with nitrogen. To this solution was added methyl chloroformate (21.5 mL, 0.28 mol) dropwise. The solution was cooled to 0° C. and stirred vigorously. To this solution was added pyridine (22.6 mL, 0.28 mol) slowly, which resulted in a very exothermic reaction and the immediate formation of a white precipitate. Upon completion (monitored via GC) (<1 hour), H$_2$O (100 mL) was added and the solution was extracted with diethyl ether (3×75 mL). The organic phases were collected and washed with 10% HCl (aq.) (3×75 mL) followed by brine solution (2×50 mL) and H$_2$O (2×50 mL). The organic phase was dried with MgSO$_4$ and the solvent was removed under reduced pressure. The resulting yellow liquid was fractionally distilled (84° C., 9.00 torr) to yield the desired colorless, pure product (35.7 g, 80.0%). Odor: weak, light, green, floral. GUNNED: m/z (%)—176(1), 161(1), 101(2), 85(43), 73(100), 69(22), 59(5), 55(12), 45(6), 43(8), 41(8). $^1$H NMR (CDCl$_3$); δ 1.17 (s, 6H), 1.86 (t, J=7.33 Hz, 2H), 3.17 (s, 3H), 3.75 (s, 3H), 4.22 (t, J=7.33 Hz, 2H). $^{13}$C NMR (CDCl$_3$): δ 25.3, 38.3, 49.3, 54.8, 64.8, 73.4, 155.9.

Example 13

This example illustrates the synthesis of 3-methoxy-3-methylbutyl prop-2-enyloxyformate.

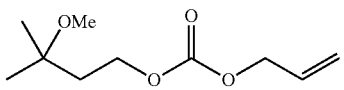

This compound was synthesized employing a procedure analogous to Example 12 using 3-methoxy-3-methyl-1-butanol (25.0 g, 0.21 mol) and allyl chloroformate (25.5 mL, 0.23 mol). The isolated crude material was fractionally distilled (86° C., 3.00 torr) resulting in a colorless, pure liquid (37.3 g, 87.0%). Odor: weak, soft chocolate, airy. GC/MS(EI): m/z (%)—202(1), 187(1), 146(1), 108(1), 101 (4), 85(45), 73(100), 69(39), 55(11), 43(8), 41(17). $^1$H NMR (CDCl$_3$); δ 1.18 (s, 6H), 1.87 (t, J=7.79 Hz, 2H), 3.18 (s, 3H), 4.23 (t, J=7.33 Hz, 2H), 4.60 (d, J=5.50 Hz, 2H), 5.25 (dd, J=10.54 Hz, 1H), 5.34 (dd, J=18.33 Hz, 1H), 5.91 (m, 1H). $^{13}$C NMR (CDCl$_3$): δ 25.3, 38.3, 49.3, 64.8, 68.4, 73.4, 118.9, 131.8, 155.1.

Example 14

This example illustrates the synthesis of 3-methoxy-3-methylbutyl propoxyformate.

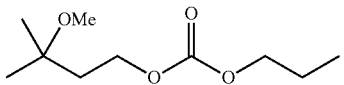

A portion of the unsaturated carbonate, 3-methoxy-3-methylbutyl prop-2-enyloxyformate, (20.0 g, 99.0 mmol) was dissolved in absolute EtOH (120 mL) and to this was added 1% (w/w) catalyst (5% Pd—C). The suspension was stirred at ambient temperature and treated with H$_2$ (250 psi) for 2 hours. Upon completion (monitored via GC), the suspension was filtered through a glass frit (M) filter packed with filter paper and celite and rinsed with ethyl acetate. The solvent was removed under reduced pressure via rotary evaporation affording a light yellow liquid which was fractionally distilled (86° C., 3.20 torr) to yield the desired colorless, pure product (18.5 g, 91.5%). Odor: weak, soft musk, light vanilla. GC/MS(EI): m/z (%)—204(1), 189(1), 101(2), 85(34), 73(100), 69(18), 55(9), 43(12), 41(12). $^1$H NMR (CDCl$_3$): 0.95 (t, J=7.79 Hz, 3H), 1.18 (s, 6H), 1.67 (m, 2H), 1.87 (t, J=7.79 Hz, 2H), 3.18 (s, 3H), 4.08 (t, J=6.87 Hz, 2H), 4.22 (t, J=7.33 Hz, 2H). $^{13}$C NMR (CDCl$_3$): δ 10.3, 22.1, 25.3, 38.3, 49.3, 64.6, 69.6, 73.6, 155.6.

Example 15

This example illustrates the synthesis of 3-methoxy-3-methylbutyl 2-methoxyacetate.

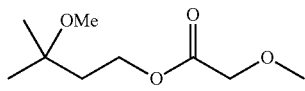

A portion of methoxyacetic acid (20 g, 0.22 mol) was dissolved in CH$_2$Cl$_2$ (160 mL) and dimethylformamide (40 mL). The solution was treated with oxalyl chloride (27.1 mL, 0.31 mol) in CH$_2$Cl$_2$ (100 mL) dropwise and stirred at room temperature for 2 hours. The temperature was then increased to 40° C. and the solution was stirred for an additional 40 minutes. The solution was then cooled to room temperature, purged with nitrogen gas for 5 minutes and then cooled to 0° C. The cooled solution was treated with a mixture of 3-methoxy-3-methyl-1-butanol (26.2 g, 0.22 mol) and pyridine (19.8 mL, 0.22 mol) in CH$_2$Cl$_2$ (50 mL) dropwise and was stirred at that temperature for 2 hours. Upon completion, 10% HCl (aq.) was added and the organic layer was washed (3×100 mL) followed by H$_2$O (100 mL). The organic phase was dried with MgSO$_4$ and the solvent was removed under reduced pressure. The resulting yellow liquid was fractionally distilled (71° C., 1.26 torr) to yield the desired colorless, pure product (25.8 g, 61.1%). Odor: weak, fruity, slight coconut, powder musk. GC/MS(EI): m/z (%)—190(1), 175(1), 128(1), 85(37), 73(100), 55(9), 45(24), 41(11). $^1$H NMR (CDCl$_3$) δ 1.17 (s, 6H), 1.84 (t, J=7.79 Hz, 2H), 3.17 (s, 3H), 3.43 (s, 3H), 4.00 (s, 2H), 4.25 (t, J=7.33 Hz, 2H). $^{13}$C NMR (CDCl$_3$): δ 25.3, 38.3, 49.3, 59.4, 61.6, 70.0, 73.5, 170.4.

Example 16

This example illustrates the synthesis of 3-methoxy-3-methylbutyl 2-ethoxyacetate.

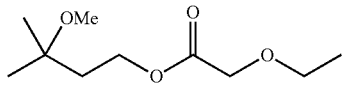

Portions of ethoxyacetic acid (50 g, 0.47 mol) and p-toluenesulfonic acid (4.50 g, 23.5 mmol) were dissolved in 3-methoxy-3-methyl-1-butanol (167 g, 1.41 mol) and stirred vigorously while heated at 40° C. for 5 hours. After this time, the solution was cooled to room temperature and diethyl ether was added (100 mL). The solution was washed with saturated NaHCO$_3$ (3×75 mL) followed by H$_2$O (100 mL). The aqueous fractions were back-extracted with diethyl ether (50 mL) and the organic layers were dried with MgSO$_4$. The solvent removed via rotary evaporation and the resulting clear liquid was fractionally distilled (70° C., 1.04 torr) to afford the desired colorless, pure product (68.4 g, 71.2%). Odor: powder musk, fresh, soft, light, clean. GC/MS(EI): m/z (%)—204(1), 189(1), 128(4), 85(32), 73(100), 59(9), 55(7), 45(7). $^1$H NMR (CDCl$_3$); δ 1.17 (s, 6H), 1.24 (t, J=6.87 Hz, 3H), 1.84 (t, J=7.33 Hz, 2H), 3.17 (s, 3H), 3.57 (q, J=7.33 Hz, 2H), 4.04 (s, 2H), 4.25 (t, J=7.79 Hz, 2H). $^{13}$C NMR (CDCl$_3$): δ 15.1, 25.3, 38.3, 49.3, 61.6, 67.3, 68.2, 73.5, 170.7.

Example 17

This example illustrates the synthesis of 3-methoxy-3-methylbutyl 2-(methylethoxy)acetate.

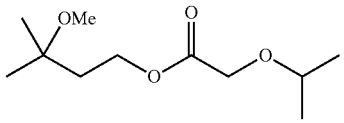

This compound was synthesized employing a procedure analogous to Example 16 using 3-methoxy-3-methyl-1-butanol (56.0 g, 0.48 mol) and methylethoxyacetic acid (14.0 g, 0.12 mol). The isolated crude material was fractionally distilled (72° C., 0.96 torr) resulting in a colorless, pure liquid (10.3 g, 39.9%). Odor: very weak powder musk. GC/MS(EI): m/z (%)—218(1), 203(1), 187(1), 160(1), 145 (1), 128(8), 101(4), 85(40), 73(100), 69(52), 55(8), 45(10), 43(24), 41(12). $^1$H NMR (CDCl$_3$): δ 1.16 (s, 6H), 1.19 (d, J=5.96 Hz, 6H), 1.83 (t, J=7.33 Hz, 2H), 3.17 (s, 3H), 3.65 (m, 1H), 4.04 (s, 2H), 4.23 (t, J=7.33 Hz, 2H). $^{13}$C NMR (CDCl$_3$): δ 21.8, 25.2, 38.5, 49.2, 61.5, 65.9, 72.6, 73.5, 170.9.

Example 18

This example illustrates the synthesis of 2-(3-methoxy-3-methylbutoxy)acetic acid.

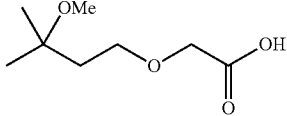

A suspension of sodium hydride (4.70 g, 0.19 mol) in anhydrous THF (100 mL) was warmed to approximately 40° C. under an inert atmosphere. A portion of 3-methoxy-3-methyl-1-butanol (20.0 g, 0.17 mol) was then added dropwise via syringe over a period of 20 minutes during which time the temperature of the mixture was slowly raised to 70° C. at 5 degree intervals. After one hour, sodium bromoacetate (28.2 g, 0.18 mol) was added in small portions over a period of 20 minutes and the mixture was stirred vigorously at 70° C. for 4 hours. Upon completion (monitored via GC), the mixture was cooled to room temperature, treated with diethyl ether (100 mL) and washed with 10% HCl (aq.) (3×75 mL) followed by brine solution (100 mL). The organic phase was dried with MgSO$_4$ and the solvent was removed under reduced pressure. The crude light yellow liquid was not purified further for use in subsequent reactions. Yield: (29.2 g, 98.0%). Odor: harsh, chemical. GC/MS (EI): m/z (%)—176(1), 161(1), 129(2), 85(30), 73(100), 69(14), 55(9), 45(7). $^1$H NMR (CDCl$_3$): δ 1.21 (s, 6H), 1.83

(t, J=5.96 Hz, 2H), 3.21 (s, 3H), 3.66 (t, J=5.96 Hz, 2H), 3.75 (s, 1H), 4.06 (s, 2H). $^{13}$C NMR (CDCl$_3$): δ 25.2, 39.3, 49.4, 68.3, 68.6, 75.0, 173.1.

Example 19

This example illustrates the synthesis of methyl 2-(3-methoxy-3-methylbutoxy)acetate.

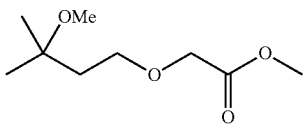

A portion of 2-(3-methoxy-3-methylbutoxy)acetic acid (Example 18) (28.0 g, 0.16 mol) was diluted with methanol (50 mL) and treated with p-toluenesulfonic acid (1.51 g, 7.95 mmol) and stirred vigorously at 40° C. for 3 hours. After this time, the solution was cooled to room temperature and diethyl ether was added (100 mL). The solution was washed with saturated NaHCO$_3$ (3×75 mL) followed by H$_2$O (100 mL). The aqueous fractions were back-extracted with diethyl ether (50 mL) and the organic layers were dried with MgSO$_4$. The solvent removed via rotary evaporation and the resulting light yellow liquid was fractionally distilled (60° C., 1.00 torr) to afford the desired colorless, pure product (18.9 g, 62.6%). Odor: metallic green, plastic. GC/MS(EI): m/z (%)—190(1), 175(1), 143(3), 99(8), 85(67), 73(100), 69(27), 55(11), 45(25). $^1$H NMR (CDCl$_3$): δ 1.16 (s, 6H), 1.84 (t, J=7.33 Hz, 2H), 3.16 (s, 3H), 3.58 (t, J=7.33 Hz, 2H), 3.73 (s, 3H), 4.06 (s, 2H). $^{13}$C NMR (CDCl$_3$): δ 25.4, 39.1, 49.2, 51.9, 68.2, 68.4, 73.7, 171.0.

Example 20

This example illustrates the synthesis of ethyl 2-(3-methoxy-3-methylbutoxy)acetate.

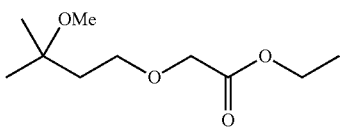

This compound was synthesized employing a procedure analogous to Example 19 using 2-(3-methoxy-3-methylbutoxy)acetic acid (14.0 g, 79.5 mmol) and ethanol (28 mL). The isolated crude material was fractionally distilled (65° C., 0.97 torr) resulting in a colorless, pure liquid (7.50 g, 46.9%). Odor: vegetable green, spicy, plastic. GC/MS(EI): m/z (%)—204(1), 189(1), 157(3), 99(10), 85(64), 73(100), 69(24), 55(9), 45(11). $^1$H NMR (CDCl$_3$): δ 1.16 (s, 6H), 1.27 (t, J=7.33 Hz, 3H), 1.84 (t, J=7.33 Hz, 2H), 3.17 (s, 3H), 3.59 (t, J=7.33 Hz, 2H), 4.04 (s, 2H), 4.20 (q, J=7.33 Hz, 2H). $^{13}$C NMR (CDCl$_3$): δ 14.3, 25.4, 39.1, 49.3, 60.9, 68.2, 68.6, 73.7, 170.6.

Example 21

This example illustrates the synthesis of methylethyl 2-(3-methoxy-3-methylbutoxy)acetate.

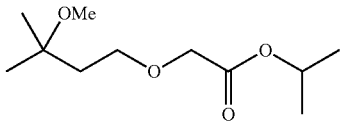

This compound was synthesized employing a procedure analogous to Example 19 using 2-(3-methoxy-3-methylbutoxy)acetic acid (28.0 g, 0.16 mol) and 2-propanol (75 mL). The isolated crude material was fractionally distilled (70° C., 0.93 torr) resulting in a colorless, pure liquid (21.4 g, 61.8 To). Odor: green, licorice, slightly mint, fresh. GC/MS (EI): m/z (%)—218(1), 203(1), 188(1), 171(1), 146(1), 129(5), 119(3), 99(12), 85(68), 73(100), 69(34), 55(9), 45(15), 43(21), 41(13). $^1$H NMR (CDCl$_3$): δ 1.17 (s, 6H), 1.25 (d, J=6.42 Hz, 6H), 1.85 (t, J=7.33 Hz, 2H), 3.17 (s, 3H), 3.60 (t, J=7.33 Hz, 2H), 4.01 (s, 2H), 5.08 (m, 1H). $^{13}$C NMR (CDCl$_3$): δ 21.9, 25.4, 39.1, 49.3, 68.2, 68.5, 68.7, 73.7, 170.2.

Example 22

This example illustrates the synthesis of 3-methoxy-3-methylbutyl 4-methylbenzenesulfonate.

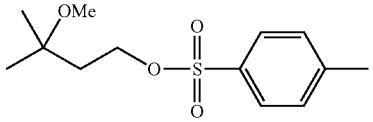 [SMILES: COC(C)(C)CCOS(=O)(=O)c1ccc(C)cc1]

A portion of p-toluenesulfonyl chloride (32.9 g, 0.17 mol) was dissolved in pyridine (50 mL) and cooled to 0° C. To this solution was added 3-methoxy-3-methyl-1-butanol (20.0 g, 0.17 mol) dropwise slowly via syringe. A white precipitate formed immediately and the mixture was stirred at 0° C. for one hour followed by an additional 3 hours at room temperature. After this time, the mixture was treated with diethyl ether (100 mL) and washed with 10% HCl (aq.) (3×75 mL), saturated NaHCO$_3$ (aq.) (2×75 mL) and H$_2$O (2×50 mL). The organic phase was dried with MgSO$_4$ and the solvent was removed under reduced pressure. The resulting crude light yellow liquid was not purified further for use in subsequent reactions. Yield: (42.0 g, 91.1%). Odor: odorless. GC/MS(EI): m/z (%)—272(1), 257(1), 207(1), 173(1), 155(4), 91(21), 85(55), 73(100), 69(17), 65(10), 55(8), 45(5), 43(6). $^1$H NMR (CDCl$_3$): δ 1.11 (s, 6H), 1.85 (t, J=7.33 Hz, 2H), 2.43 (s, 3H), 3.08 (s, 3H), 4.11 (t, J=7.33 Hz, 2H), 7.33 (d, J=8.25 Hz, 2H), 7.77 (d, J=8.25 Hz, 2H). $^{13}$C NMR (CDCl$_3$): δ 21.7, 25.2, 38.8, 49.3, 67.4, 73.3, 128.0, 129.9, 133.2, 144.8.

Example 23

This example illustrates the synthesis of 1-methoxy-3-(3-methoxy-3-methylbutoxy)-1,1-dimethylpropane.

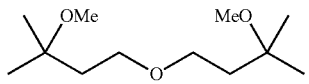

A suspension of sodium hydride (2.35 g, 93.1 mmol) in anhydrous THF (60 mL) was warmed to approximately 40° C. under an inert atmosphere. A portion of 3-methoxy-3-methyl-1-butanol (10.0 g, 84.6 mmol) was then added dropwise via syringe over a period of 20 minutes during which time the temperature of the mixture was slowly raised to 70° C. at 5 degree intervals. After one hour, the sulfonate product from Example 22 (23.0 g, 84.6 mmol) was added in small portions After this time, the mixture was cooled to room temperature, treated with diethyl ether (100 mL) and washed with saturated $NaHCO_3$ (aq.) (2×100 mL) followed by brine solution (2×50 mL). The organic phase was dried with $MgSO_4$ and the solvent was removed under reduced pressure. The resulting light yellow liquid was fractionally distilled (73° C., 0.95 torr) to yield the desired colorless, pure ether (13.2 g, 71.7%). Odor: mold, mildew. GC/MS (EI): m/z (%)—218(1), 171(1), 154(2), 139(21), 115(3), 99(10), 85(39), 73(100), 69(36), 55(9), 45(18), 43(14), 41(12). $^1H$ NMR ($CDCl_3$); δ 1.15 (s, 12H), 1.77 (t, J=7.33 Hz, 4H), 3.17 (s, 6H), 3.47 (t, J=7.33 Hz, 4H). $^{13}C$ NMR ($CDCl_3$): δ 25.5, 39.3, 49.2, 67.2, 73.8.

Example 24

This example illustrates the synthesis of 1-methoxy-1,1-dimethyl-3-(1-methylprop-2-enyloxy)propane.

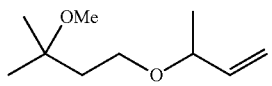

This compound was synthesized employing a procedure analogous to Example 23 using 3-methoxy-3-methylbutyl 4-methylbenzenesulfonate (37.9 g, 0.14 mol) and 3-butene-2-ol (12.4 mL, 0.14 mol). The isolated crude material was fractionally distilled (40° C., 2.45 torr) resulting in a colorless, pure liquid (14.0 g, 58.6%). Odor: strong, mint, citrus, rose. GC/MS(EI): m/z (%)—172(1), 157(1), 117(1), 95(3), 85(14), 73(100), 69(12), 55(33), 45(6), 41(8). $^1H$ NMR ($CDCl_3$): δ 1.15 (s, 6H), 1.22 (d, J=5.96 Hz, 3H), 1.77 (m, 2H), 3.16 (s, 3H), 3.37 (dq, J=9.16 Hz, 1H), 3.52 (dq, J=8.71 Hz, 1H), 3.79 (t, J=6.87 Hz, 1H), 5.10 (d, J=12.37 Hz, 1H), 5.16 (d, J=16.95 Hz, 1H), 5.72 (dt, J=7.33 Hz, 1H). $^{13}C$ NMR ($CDCl_3$): δ 21.4, 25.5, 39.4, 49.2, 64.5, 73.9, 115.6, 140.6.

Example 25

This example illustrates the synthesis of 2-(3-methoxy-3-methylbutoxy)prop anal.

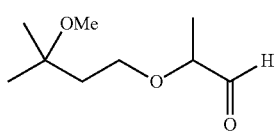

A portion of 1-methoxy-1,1-dimethyl-3-(1-methyl prop-2-enyloxy)propane (5.75 g, 33.3 mmol) was dissolved in $CH_2Cl_2$ (50 mL) and cooled to −78° C. The solution was purged with ozone for approximately one hour. Once the solution became blue, $O_2$ was bubbled through it for 30 minutes until the color disappeared and the reaction was quenched via addition of triphenylphosphine (10.5 g, 40.0 mmol). The solvent was removed via rotary evaporation and the resulting residue was suspend in a hexane:diethyl ether (1:1) mixture overnight in the refrigerator. The mixture was filtered and the precipitate was rinsed with hexane. The filtrate was placed on a rotary evaporator and the solvent was removed under reduced pressure. The isolated crude material was distilled via Kugelrohr apparatus (64° C., 0.40 torr) resulting in a colorless liquid (4.57 g, 78.8%). Odor: fresh, watery melon, clean, floral, muguet. GC/MS(EI): m/z (%)—174(1), 159(1), 145(1), 127(3), 113(36), 101(5), 85(24), 73(100), 69(75), 59(41), 57(14), 55(11), 45(26), 43(19), 41(22). $^1H$ NMR ($CDCl_3$): δ 1.17 (s, 6H), 1.27 (d, J=6.87 Hz, 3H), 1.84 (dt, J=6.42 Hz, 2H), 3.18 (s, 3H), 3.61 (m, 2H), 3.76 (dq, J=8.71 Hz, 1H), 9.64 (d, J=1.83 Hz, 1H). $^{13}C$ NMR ($CDCl_3$): δ 15.3, 25.4, 39.6, 49.3, 66.5, 73.7, 80.5, 204.0.

Example 26

This example illustrates the synthesis of 2-(3-methoxy-3-methylbutoxy)ethanal.

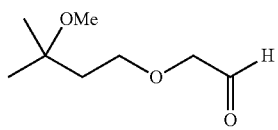

A portion of the dimethyl acetal, 3-(2,2-dimethoxy-ethoxy)-1-methoxy-1,1-dimethylpropane (Example 1), (27.6 g, 0.13 mol) was dissolved in a large excess of neat formic acid (74.0 g, 1.61 mol) and stirred vigorously for 4 hours. Upon completion (monitored via GC), the solution was treated with $H_2O$ (150 mL) and extracted with ethyl acetate (3×100 mL). The organic phases were collected and dried with $MgSO_4$ and the solvent was removed under reduced pressure. The resulting light yellow liquid was carefully distilled via Kugelrohr apparatus first to remove any leftover formic acid (25° C., 1.00 torr) followed by isolation of the desired aldehyde (40° C., 0.10 torr) resulting in a colorless, pure liquid (13.0 g, 60.2%). Odor: fresh, melon, clean, floral, muguet, green. GC/MS(EI): m/z (%)—161(1), 145(2), 113(1), 99(6), 85(29), 73(100), 69(27), 55(9), 45(23), 43(14), 41(11). $^1H$ NMR ($CDCl_3$); δ 1.17 (s, 6H), 1.85 (t, J=7.33 Hz, 2H), 3.17 (s, 3H), 3.61 (t, J=7.33 Hz, 2H), 4.06 (s, 2H), 9.71 (s, 1H). $^{13}C$ NMR ($CDCl_3$): δ 25.4, 39.3, 49.3, 68.4, 73.7, 76.5, 201.0.

Example 27

This example illustrates the synthesis of 3-(3-methoxy-3-methylbutoxy)propanal.

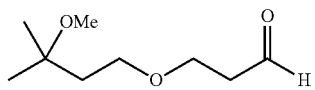

A portion of 3-methoxy-3-methyl-1-butanol (10.0 g, 84.6 mmol) was treated with acrolein (25.1 mL, 0.34 mol) and a small aliquot of concentrated HCl (7 drops). The solution was stirred vigorously at 40° C. in subdued light for 3 days. After this time, the solution was cooled to room temperature and ethyl acetate (75 mL) was added. The solution was washed with saturated NaHCO$_3$ (aq.) (100 mL) followed by H$_2$O (50 mL). The organic phase was dried with MgSO$_4$ and the solvent was removed under reduced pressure. The resulting light yellow liquid was distilled (58° C., 0.92 torr) to yield the desired colorless aldehyde (8.21 g, 55.9%). Odor: waxy, oily, muguet, light floral. GC/MS(EI): m/z (%)—174 (1), 159(1), 127(5), 85(19), 73(100), 69(7), 57(9), 55(8), 45(12), 43(11). $^1$H NMR (CDCl$_3$): δ 1.14 (s, 6H), 1.76 (t, J=7.33 Hz, 2H), 2.64 (dt, J=4.12 Hz, 2H), 3.16 (s, 3H), 3.51 (t, J=7.33 Hz, 2H), 3.74 (t, J=5.96 Hz, 2H), 9.77 (t, J=2.29 Hz, 1H). $^{13}$C NMR (CDCl$_3$): δ 25.4, 39.2, 44.0, 49.2, 64.6, 67.6, 73.8, 201.4.

Example 28

This example illustrates the synthesis of 3-(3-methoxy-3-methylbutoxy)butanal.

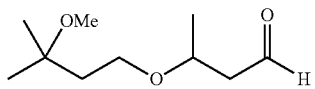

This compound was synthesized employing a procedure analogous to Example 27 using 3-methoxy-3-methyl-1-butanol (10.0 g, 84.6 mmol) and crotonaldehyde (42.9 mL, 0.51 mol). The isolated crude material was fractionally distilled (48° C., 0.35 torr) resulting in a colorless liquid (3.24 g, 20.4%). Odor: waxy, oily, fatty. GC/MS(EI): m/z (%)—188(1), 173(1), 141(3), 101(5), 85(18), 73(100), 69(11), 55(7), 43(20), 41(15). $^1$H NMR (CDCl$_3$): δ 1.14 (s, 6H), 1.23 (d, J=6.42 Hz, 3H), 1.74 (t, J=6.87 Hz, 2H), 2.45 (qd, J=22.91 Hz, 1H), 2.60 (qd, J=26.12 Hz, 1H), 3.17 (s, 3H), 3.43 (m, 1H), 3.60 (m, 1H), 3.93 (m, 1H), 9.77 (t, J=2.29 Hz, 1H). $^{13}$C NMR (CDCl$_3$): δ 19.9, 25.4, 39.6, 49.2, 50.6, 64.9, 71.0, 73.8, 201.7.

Example 29

This example illustrates the synthesis of bis(3-methoxy-3-methylbutyl ethane)-1,2-dioate.

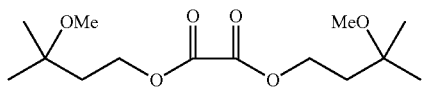 [SMILES: COC(C)(C)CCOC(=O)C(=O)OCCC(C)(C)OC]

A portion of 3-methoxy-3-methyl-1-butanol (5.00 g, 42.3 mmol) was dissolved in CH$_2$Cl$_2$ (25 mL) and cooled to 0° C. An aliquot of oxalyl chloride (2.21 mL, 25.4 mmol) was slowly added dropwise via syringe to the vigorously stirring solution. After one hour, the solution was warmed to room temperature and washed with saturated NaHCO$_3$ (aq.) (2×50 mL) followed by brine solution (30 mL) and H$_2$O (30 mL). The organic phase was dried with MgSO$_4$ and the solvent was removed under reduced pressure. The resulting clear liquid was distilled via kugelrohr apparatus (160° C., 0.15 torr) to yield the desired colorless, viscous oxalate (4.50 g, 73.3%). Odor: weak, chemical. GC/MS(EI): m/z (%)—290 (1), 275(1), 257(1), 227(1), 191(1), 159(1), 101(2), 85(37), 73(100), 69(21), 55(6), 43(7), 41(9). $^1$H NMR (CDCl$_3$): δ 1.19 (s, 12H), 1.91 (t, J=7.33 Hz, 4H), 3.18 (s, 6H), 4.37 (t, J=7.79 Hz, 4H). $^{13}$C NMR (CDCl$_3$): δ 25.3, 37.9, 49.4, 63.8, 73.5, 158.0.

The below examples demonstrate the use of the fragrance formulation of Table 2 in various consumer products. These examples are illustrative only and are not intended to limit the scope of the invention in any way. Unless otherwise noted, all percentages set forth in the examples are by weight (wt). Q.S. means a sufficient quantity.

Example 30: All Purpose Cleaner—Concentrated

| Ingredient | Supplier | Percentage | Purpose |
|---|---|---|---|
| Neodol ® 91-8 | Shell | 6.00 | Surfactant |
| Dowanol ® DPnB | Dow | 6.00 | Solvent |
| Kathon ® CG | Rohm & Haas | 0.10 | Preservative |
| Fragrance of Table 2 | Takasago Int'l | 1.25 | Fragrance |
| D. I. Water | — | 86.65 | Solvent |
| Dye | Pylam | Q.S. | Color |

This formulation is for dilution in a bucket at approximately one part concentrate to ten parts tap water.

Procedure:

1. The Neodol® 91-8, Dowanol® DPnB, and fragrance were mixed in a suitable vessel until completely uniform and clear.

2. Water was added slowly with constant agitation to the solution in #1. Kathon® was added with mixing and stirring continued for 1 minute. The final formulation was clear.

3. Dye was added match standard.

Example 31: Hard Surface Cleaner—Pump Spray

| Ingredient | Supplier | Percentage | Purpose |
|---|---|---|---|
| Neodol ® 91-8 | Shell | 1.50 | Surfactant |
| Dowanol ® DPnB | Dow | 4.00 | Solvent |
| Fragrance of Table 2 | Takasago Int'l | 0.40 | Fragrance |
| Kathon ® CG | Rohm & Haas | 0.07 | Preservative |
| D. I. Water | — | 94.03 | Solvent |

Procedure:

1. Neodol® 91-8, Dowanol® DPnB, and fragrance were mixed in a suitable vessel until completely uniform and clear.

2. Water was added slowly to the solution in #1 with constant agitation. The final formulation was clear. Kathon® CG was added with stirring.

The formulation was then filled into suitable plastic containers (PET preferred), with the proper trigger or pump closure.

Example 32: Liquid Laundry Detergent

| Ingredient | INCI or Nomenclature | Percentage |
|---|---|---|
| Water | Water | Q.S. |
| Glucopon ® 625UP (1) | Alkyl Polyglucosides | 12.50 |
| Standapol ® ES-40 (1) | Alkyl Ether Sulfates | 25.60 |
| Versene ® 100 (38%) (2) | Tetrasodium EDTA | 00.40 |
| MBA (2) | Monoethanolamine | 01.00 |
| Sulfuric Acid (25% Aq.) | Acid | 03.00 |

-continued

| Ingredient | INCI or Nomenclature | Percentage |
|---|---|---|
| Sodium Chloride (25%) | Salt | 01.20 |
| Takasago Fragrance(3) | Fragrance of Table 2 | 00.75 |
| | | 100.00 |

Suppliers
(1) Cognis Corporation
(2) The DOW Chemical Co.
(3) Takasago International Corporation Procedure:
1. Glucopon® was added to water heated to 65° C. and mix at medium speed until clear.
2. Standapol® was added and mixing continued until the mixture was clear and homogenous.
3. The mixture was removed from the heat and remaining ingredients were added in order, with mixing at slow to medium speed each addition.
4. pH was adjusted with sulfuric acid solution to pH of 8.0 to 8.5.
5. Viscosity was adjusted with sodium chloride.

Example 33: Liquid Fabric Softener

| Ingredient | Supplier | Percentage | Purpose |
|---|---|---|---|
| Deionized Water | — | 83.50 | Solvent |
| Rewoquat® WE-16E | Degussa | 15.00 | Softener |
| Sodium Chloride | — | 0.50 | Thickening |
| Fragrance of Table 2 | Takasago | 1.00 | Fragrance |

Procedure:
1. Rewoquat®, fragrance and water were mixed in a suitable vessel until the mixture was translucent to opaque.
2. Sodium chloride was added with mixing and mixed for 5 minutes.

Example 34: Hand & Body Lotion

| SEQ. | INGREDIENTS | | INCI or Nomenclature | PERCENT |
|---|---|---|---|---|
| Part 1 | | | | |
| 1 | Deionized water | | Water | QS |
| 1 | Versene® 220 | (1) | Tetrasodium EDTA | 00.05 |
| 2 | Carbopol® 934 | (2) | Carbomer 934 | 00.30 |
| 3 | Glycerin | | Glycerin | 01.00 |
| 3 | Propylene Glycol | | Propylene Glycol | 01.00 |
| Part 2 | | | | |
| 4 | Myrj® 52S (sprayed) | (4) | PEG-40 Stearate | 01.80 |
| 4 | Liponate® GC | (5) | Caprylic/Capric Triglyceride | 13.00 |
| 4 | Liponate® IPM | (5) | Isopropyl Myristate | 08.50 |
| 4 | Span® 65S (sprayed) | (4) | Sorbitan Tristearate | 02.00 |
| 4 | Pharmalan®, USP | (6) | Lanolin | 00.50 |
| 4 | White Protopet® IS | (7) | Petrolatum | 00.30 |
| 4 | Propylparaben | (8) | Propylparaben | 00.10 |
| Part 3 | | | | |
| 1 | Deionized Water | | Water | 10.00 |
| 1 | TEA | | Triethanolamine | 00.30 |
| Part 4 | | | | |
| 1 | Deionized Water | | Water | 01.00 |
| 1 | Unicide® U-13 | (5) | Imidazolidinyl Urea | 00.25 |
| Part 5 | | | | |
| 1 | Germaben® II | (3) | Propylene Glycol (and) Diazo-lidinyl Urea (and) Methylparaben (and) Propylparaben | 00.70 |
| Part 6 | | | | |
| 1 | Takasago Fragrance Oil | | Fragrance of Table 2 | QS |

Suppliers:
(1) Dow Chemical
(2) Noveon
(3) Sutton/ISP
(4) Uniqema
(5) Lipo Chemicals, Inc.
(6) Croda
(7) Crompton/Witco
(8) Tri-K Procedure:
Part 1
1. Seq. #1 was heated to 75° C. and mixed together at medium speed using an overhead mixer until clear.
2. Seq. #2 was added slowly to Seq. #1 with mixing. Mixing was continued until Seq. #2 is completely was hydrated. Hydration was checked by dipping a metal spatula into and out of the solution to observe if there are any gum particles that have not hydrated.
3. Seq. #3 was added in order to the batch without heating.
Part 2
4. Seq. #4 was premixed and heated until completely melted at approximately 65° C.
5. Part 1 was placed on a Homomixer at low to medium speed, and Part 2 added to Part 1 and mixed for 1 minute.
6. The batch was placed back onto the overhead mixer at medium speed and premixed Part 3 was added without heating to the batch for approximately 2 minutes.
7. Mix was continued at low speed and the mixture was cooled to 35° C.
8. Part 4 was premixed at 35° C. and added to the batch, while cooling down at low speed to 30° C.
9. Part 5 was added at 30° C. with mixing at low speed. Liquid fragrance was added slowly while mixing.
10. Lotion was placed in jars and allowed to at room temperature for 24 hours.

Example 35: Clear Liquid Hand Soap

| SEQ. | INGREDIENTS | | INCI | PERCENT |
|---|---|---|---|---|
| 1 | Deionized water | | Water | 66.50 |
| 1 | Methyl Paraben | (1) | Methyl Paraben | 00.25 |
| 2 | Liponic® EG-1 | (2) | Glycereth-26 | 01.00 |
| 2 | Glycerin | (3) | Glycerin | 01.00 |
| 2 | Lipopeg® 6000DS | (2) | PEG-150 Distearate | 00.50 |
| 3 | Monamid® 716 | (4) | Lauramide DEA | 03.50 |
| 3 | Standapol® ES-2 | (3) | Sodium Laureth Sulfate | 25.00 |
| 3 | Velvetex® BK-35 | (3) | Cocamidopropyl Betaine | 15.00 |

-continued

| SEQ. | INGREDIENTS | | INCI | PERCENT |
|---|---|---|---|---|
| 4 | Deionized Water | | Water | 01.00 |
| 4 | Unicide ® U-13 | (2) | Imidazolidinyl Urea | 00.25 |
| 5 | Fragrance as defined in Table 2 above | | | 00.50 |
| 6 | Citric acid (25% Solution) | | | QS |

Suppliers:
(1) TRI-K
(2) Lipo Chemicals, Inc.
(3) Cognis/Henkel
(4) Uniqema

Procedure:

1. The methyl paraben was added slowly to the DI water heated to 65° C. with mixing at medium/high speed using an overhead mixer until completely into solution and clear. (Seq.#1)

2. Seq. #2 was added to Sequence #1 at low speed until completely clear.

3. Seq. #3 was added to batch without heating, in order of addition, and cooled down to 35° C. with low agitation.

4. Seq. #4 was premixed until clear, and added to batch.

5. Seq. #5 was added to the batch with low agitation and cooled down to 25° C.

6. Seq. #6 was added to adjust batch to desired pH. The product was placed in jars, pouring very slowly onto the sides of the jars to eliminate any additional aeration. pH=adjust to: 6.64+/−0.2; viscosity=18,640 cps (+/−10%) with Brookfield LV Sp. #4 @ 30 rpm Example 36: Clear Shampoo

| SEQ. | INGREDIENTS | | INCI | PERCENT |
|---|---|---|---|---|
| 1 | Deionized water | | Water | Q.S. |
| 2 | Versene ® 220 | (1) | Teterasodium EDTA | 00.05 |
| 3 | Methocel ® E4M (*prep) | (2) | Hydroxypropyl Methylcellulose | 00.30 |
| 4 | Standapol ® T | (3) | TEA Lauryl Sulfate | 18.00 |
| 4 | Standapol ® A | (3) | Ammonium Lauryl Sulfate | 08.00 |
| 4 | Monamid ® 150-LMWC | (4) | Lauramide DEA | 04.00 |
| 4 | Palmitic Acid | (5) | Palmitic Acid | 00.30 |
| 5 | Glydant ® 2000 | (6) | DMDM Hydantoin | 00.15 |
| 5 | Sodium Chloride, Granular | (7) | Sodium hloride | 00.34 |
| 5 | Citric Acid | (8) | Citric Acid | 00.43 |
| 6 | Takasago perfume oil | (9) | Fragrance of Table 2 | Q.S. |

Suppliers:
(1) AND
(2) DOW CHEMICAL CO.
(3) COGNIS/HENKEL
(4) UNIQEMA
(5) Takasago International Corp (TIC), USA
(6) LONZA
(7) FISHER SCIENTIFIC
(8) TIC, USA
(9) TIC, USA Procedure: 1. ⅓ of Seq.#1 and Seq.#2 was heated to 85° C. Methocel powder was by mixing thoroughly using ⅕ to ⅓ of the required total amount of water as hot water (80-90° C.). Mixing was continued with overhead mixer at medium speed until all of the particles were wetted down, and a consistent dispersion was obtained. The remainder of the water containing Seq. #2 was added as cold water while mixing. The solution was cooled down to less than 30° C. Mixing was continued after the proper temperature was achieved for approximately 20 minutes. After preparation was completed, the Methocel® solution was reheated to 60° C.

2. Seq.#4 at 60 to 65° C. was added slowly to the batch in order of addition with mixing continued at low speed.

3. Seq.#5 was added slowly to batch and mixing continued at low speed until room temperature was reached. Citric acid was added to a pH of 5.5-6.0 and sodium chloride was added to achieve the desired viscosity. Fragrance Seq.#6 was weighed and added to the formulation while mixing.

4. Viscosity: =2020 cps. (±10%) taken at 20° C., (Brookfield LV Sp.#3 @ 12 rpm), pH=5.5 (+/−0.5)

The below examples demonstrate the use of the materials claimed in flavor formulations in various consumer products. These examples are illustrative only and are not intended to limit the scope of the invention in any way. In these examples, all % are % (wt), unless otherwise noted and Q.S. means a sufficient quantity.

Example 37: Tooth Paste

Toothpaste with flavor and the claimed compound(s) was prepared according to the formulation below.

| Components | WT % |
|---|---|
| 2-(3-methoxy-3-methylbutoxy)ethanal [Compound 23; TABLE 1] | 0.50 |
| Calcium hydrogen phosphate (dihydrate) | 50.00 |
| Glycerin | 25.00 |
| Sodium lauryl sulfate | 1.40 |
| Carboxymethyl cellulose sodium salt | 1.50 |
| Saccharin sodium salt | 0.20 |
| Sodium benzoate | 0.10 |
| Strawberry type flavor | 0.70 |
| Purified water balance | qs |
| Total | 100.00 |

Example 38: Peach Flavor

Peach flavor utilizing the claimed compound(s) was prepared according to the formulation below utilizing the claimed compounds.

| Components | WT % |
|---|---|
| 2-(3-methoxy-3-methylbutoxy)ethanal [Compound 23; TABLE 1] | 0.20 |
| Benzaldehyde | 0.20 |
| methyl cyclohexyl)ethanone | 0.30 |
| Ethyl acetate | 2.0 |
| Ethyl butyrate | 0.8 |
| Ethyl maltol | 0.3 |
| γ-Undecalactone | 0.5 |
| Linalool | 0.5 |
| Peach flavor base | 5.0 |
| Ethyl alcohol balance | q.s. |
| Total | 100.00 |

Example 39: Green Tea Flavor

Green tea flavor was prepared according to the formulation below utilizing the claimed compound(s)

| Components | WT % |
|---|---|
| Benzyl alcohol | 1.0 |
| 2-(3-methoxy-3-methylbutoxy)ethanal [Compound 23; TABLE 1] | 0.3 |
| Cis-3-hexenol | 0.3 |
| Dimethyl sulfide | 0.1 |
| Geraniol | 0.6 |
| 1-menthol | 2.5 |
| Linalool | 0.9 |
| Nerolidol | 0.2 |
| Terpineol | 0.2 |
| Green tea base | 5.0 |
| Ethyl alcohol balance | qs |
| Total | 100.00 |

Example 40: Black Tea Flavor

Black tea flavor was prepared according to the formula below utilizing the claimed compounds.

| Components | WT % |
|---|---|
| α-Ionone | 0.2 |
| α-Ionone | 0.2 |
| Benzaldehyde | 1.0 |
| 2-(3-methoxy-3-methylbutoxy)ethanal [Compound 23; TABLE 1] | 1.0 |
| Cis-3-hexenol | 6.0 |
| δ-Decalactone | 2.5 |
| δ-Dodecalactone | 2.0 |
| Damascenone | 0.1 |
| Linalool | 3.5 |
| Geraniol | 6.0 |
| Citral | 1.0 |
| Linalool oxide | 1.6 |
| Methyl salicylate | 2.0 |
| Phenylethyl alcohol | 6.0 |
| Hexyl aldehyde | 1.0 |
| Propylene glycol balance | qs |
| Total | 100.00 |

What is claimed is:

1. A fragrance composition comprising:
a compound represented by the formula (VI):

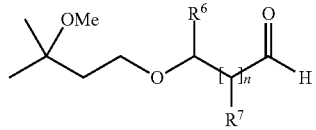

wherein
$R^6$ and $R^7$ are, independently, a hydrogen or an unsubstituted or substituted $C_{1-6}$ straight chain alkyl, an unsubstituted or substituted $C_{3-6}$ branched chain alkyl group and n=0-1; and
a fragrance carrier or fragrance base.

2. The composition of claim 1, wherein the compound is present in an amount from about 0.001% to about 30% by weight.

3. The composition of claim 1, wherein the fragrance carrier is an emulsifying agent, an encapsulating material, natural or modified starches, polymers, gums, pectins, gelatinous or porous cellular materials, or waxes.

4. A consumer product comprising the composition of claim 1.

5. The consumer product of claim 4, where the consumer product is an air care product, candle, perfume, cologne, personal care product, cosmetic, detergent, fabric care product, or household cleaning agent.

6. A method of improving, enhancing, or modifying the olfactory properties of a product comprising adding to the product an olfactory effective amount of a fragrance composition comprising:
a compound represented by the formula (VI):

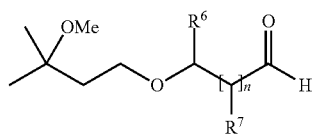

wherein $R^6$ and $R^7$ are, independently, a hydrogen or an unsubstituted or substituted $C_{1-6}$ straight chain alkyl, an unsubstituted or substituted $C_{3-6}$ branched chain alkyl group and n=0-1; and
a fragrance carrier or fragrance base.

7. The method of claim 6, wherein the olfactory effective amount is from about 0.001% to about 30% by weight.

* * * * *